(12) United States Patent
Puthiaparampil et al.

(10) Patent No.: US 8,207,346 B2
(45) Date of Patent: Jun. 26, 2012

(54) METHODS OF SYNTHESIZING ANATABINE

(75) Inventors: Tom Thomas Puthiaparampil, Bangalore (IN); Thomas Kanathkunn David, Bangalore (IN); Muppala Sarveswara Raju, Bridgewater, NJ (US)

(73) Assignee: Rock Creek Pharmaceuticals, Inc., Gloucester, MA (US)

( * ) Notice: Subject to any disclaimer, the term of this patent is extended or adjusted under 35 U.S.C. 154(b) by 207 days.

(21) Appl. No.: 12/729,346

(22) Filed: Mar. 23, 2010

(65) Prior Publication Data

US 2011/0237627 A1    Sep. 29, 2011

(51) Int. Cl.
C07D 401/00    (2006.01)
A61K 31/44    (2006.01)

(52) U.S. Cl. .................................. 546/268.1; 514/332

(58) Field of Classification Search .................. None
See application file for complete search history.

(56) References Cited

FOREIGN PATENT DOCUMENTS

| EP | 0567251 A1 | 10/1993 |
|----|------------|---------|
| WO | 9962531 A1 | 12/1999 |
| WO | 02076434 A2 | 10/2002 |
| WO | 2010030887 A1 | 3/2010 |

OTHER PUBLICATIONS

Deo, N. et al Tetrahedron Letters 1996, vol. 37, pp. 1137-1140.*
Fu-Dong Shi et al: "Nicotinic attenuation of central nervous system inflammation and autoimmunity." Feb. 1, 1999, Journal of Immunology, 1950, vol. 182, Nr. 3, pp. 1730-1739.
Travis T. Denton et al., "Nicotine-related alkaloids and metabolites as inhibitors of human cytochrome P-450 2A6.", Feb. 15, 2004, Biochemical Pharmacology, Vo. 67. Nr 4, pp. 751-756.
Allan R. Brasier, "The NF-kappaB regulatory network," 2006, Cardiovascular Toxicology 2006, vol. 6, Nr. 2, pp. 111-130.
F.X. Felpin et al., "Total synthesis of (S)-anabasine and (S)-anatabine", 2000, Synlett 2000 DE, Nr. 11, pp. 1646-1648.
F.X. Felpin et al., "Efficient enantiomeric synthesis of pyrrolidine and piperidine alkaloids from tobacco,", Sep. 21, 2001, The Journal of Organic Chemistry Sep. 21, 2001, vol. 66, Nr. 19, pp. 6305-6312.
Deo et al., "Regioselective alkylation of N-(diphenylmethylidine)-3-(aminomethyl)pyridine: A simple route to minor tobacco alkaloids and related compounds," Tetrahedron Letters, vol. 37, Issue 8, Feb. 19, 1996, pp. 1137-1140.
Crooks PA. "Chemical properties of nicotine and other tobacco-related compounds." In: Gorrod JW, Jacob P, editors. Analytical Determination of Nicotine and Related Compounds and Their Metabolites. New York, NY: Elsevier; 1999. pp. 69-147.
Ayers, Joshua T. et al., "A General Procedure for the Enantioselective Synthesis of the Minor Tobacco Alkaloids Nornicotine, Anabasine, and Anatabine," The AAPS Journal 2005; 7 (3) Article 75 (http://www.aapsj.org) (pp. E752-E758).
Datasheet 219704, (R,S)-Anatabine Tartrate (2:3) sc-219704; http://www.scbt.com/datasheet-219704-r-s-anatabine-tartrate-2-3.html (printed: Aug. 26, 2010).

* cited by examiner

Primary Examiner — Janet Andres
Assistant Examiner — Heidi Reese
(74) Attorney, Agent, or Firm — Banner & Witcoff, Ltd.

(57) ABSTRACT

Anatabine is obtained by reacting benzophenoneimine with 3-aminomethyl pyridine to form benzylhydrylidene-pyridin-3-yl-methyl-amine. The benzylhydrylidene-pyridin-3-yl-methyl-amine is treated with a non-nucleophilic base and a dielectrophile, such as cis-1,4-dichloro-2-butene, followed by acidification, then basification, to provide anatabine. The resulting anatabine is substantially free from contaminants and displays good stability. In an alternative embodiment, the benzylhydrylidene-pyridin-3-yl-methyl-amine may be used in the synthesis of other alkaloids such as anabasine, nornicotine, N-methylanabasine, and anabaseine.

2 Claims, 4 Drawing Sheets

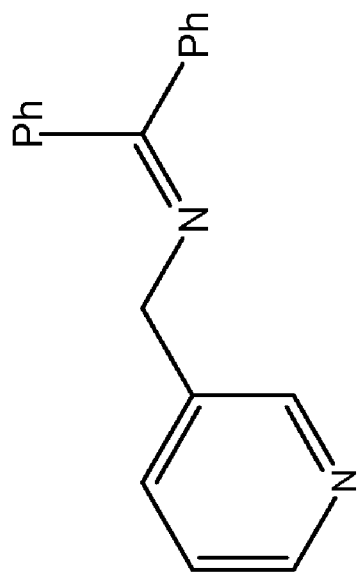
Formula I
Step 2-i →
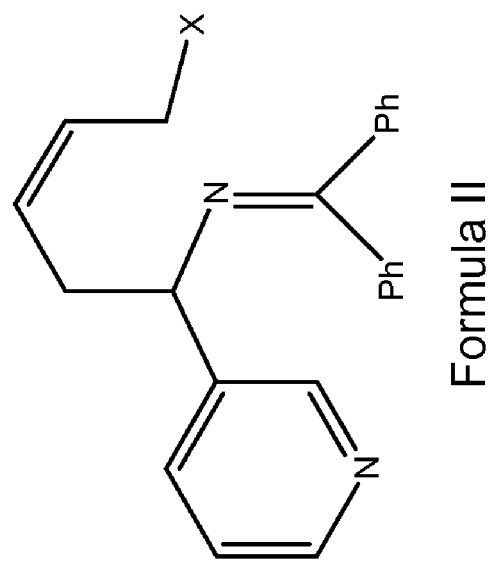
Formula II
Figure 2

METHODS OF SYNTHESIZING ANATABINE

BACKGROUND

Anatabine is among the pharmacologically active alkaloids present in tobacco and a variety of foods, including green tomatoes, green potatoes, ripe red peppers, tomatillos and sundried tomatoes albeit, in low concentrations. Anatabine is known to inhibit monoamine oxidase (MAO), an activity beneficial for treating depression and various other disorders. See, for example, Williams et al. U.S. Pat. No. 6,929,811.

Anatabine may be extracted from tobacco and presumably from other sources in the food supply or prepared synthetically as described in Deo et al., "Regioselective Alkylation of N-(diphenylmethylidene)-3-(aminomethyl)pyridine: A Simple Route to Minor Tobacco Alkaloids and Related Compounds," Tetrahedron Letters, Vol. 37, No. 8, February 1996, 1137-1140. Deo et al. discloses reacting 3-aminomethylpyridine with benzophenone in benzene to produce a Schiff base. The benzene is replaced with THF (tetrahydrofuran) then the solution is treated with LDA (lithium diisopropylamide) at −78° C. followed by addition of a dielectrophile to form an α-alkylated imine. The resulting α-alkylated imine was hydrolyzed by addition of hydrochloric acid (HCl) and the resulting solution was treated with solid $K_2CO_3$ and a KOH solution, forming the desired piperidine or pyrolidine analog. Using cis-1,4-dichloro-2-butene as the dielectrophile afforded anatabine on a small-scale (105 mg) in a yield of 65 to 75%. Deo et al. do not provide for larger scale (e.g., commercial) production of anatabine. In addition, the method uses benzene, a hazardous material, for water removal. Water removal requires large volumes of benzene and elevated temperatures, which limit the ability to scale up the process and/or make it commercially untenable.

Analysis of the resulting solution prepared according to the method of Deo et al. showed that benzophenone was present as a contaminant at about 8-12%, which was unacceptably high for use in pharmaceuticals, dietary supplements or as a food-grade salt because of the potential for carry over of this impurity in the final product. Further, Deo et al. report that the reaction of benzophenone and 3-aminomethylpyridine takes 12-16 hours to complete.

There is a need in the art for anatabine synthesis methods having better yields and stability, especially cost-effective methods that facilitate larger scale production.

SUMMARY

In one aspect of this invention, a method is provided to prepare benzylhydrylidene-pyridin-3-ylmethyl-amine (Formula I) by reacting 3-aminomethylpyridine with benzophenoneimine, or benzophenoneimine substituted in one or both aromatic rings.

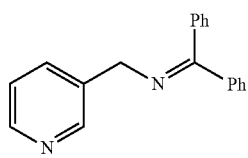

Formula I

In another aspect, a method is provided to synthesize anatabine. Benzylhydrylidene-pyridin-3-ylmethyl-amine (Formula I) is prepared by reacting 3-aminomethylpyridine with benzophenoneimine, or benzophenoneimine substituted in one or both aromatic rings. The compound of Formula I is reacted with a non-nucleophilic base and a dielectrophile to obtain a compound of Formula II.

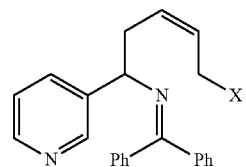

Formula II

The compound of Formula II is then acidified to provide a compound of Formula III.

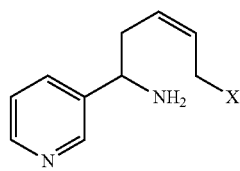

Formula III

The compound of Formula III is basified to yield anatabine.

In another aspect, a novel method is provided to recover anatabine from a reaction product by contacting the reaction product with methyl t-butyl ether (MTBE). Subsequence distillation yields anatabine with a purity greater than 99%.

In yet another aspect, acceptable pharmaceutical or food-grade salts of anatabine are prepared.

In an alternative embodiment, methods are provided for synthesizing other minor alkaloids, such as anabasine, nornicotine, N-methylanabasine, or anabaseine. A compound of Formula I may be prepared as previously described and reacted with a dielectrophile to yield a compound of Formula IIa:

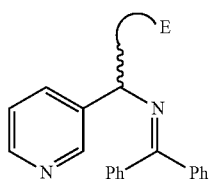

Formula IIa

The dielectrophile may be selected according to the desired alkaloid. The compound of Formula IIa is then acidified to provide a compound of Formula IIIa.

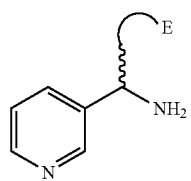

Formula IIIa

Basification of the compound of Formula IIIa results in the desired alkaloid by intramolecular N-alkylation.

BRIEF DESCRIPTION OF THE DRAWINGS

FIG. 2 illustrates step 2i of the reaction. The benzylhydrylidene-pyridin-3-yl-methyl-amine is converted to Formula II.

DETAILED DESCRIPTION

Figure 1:
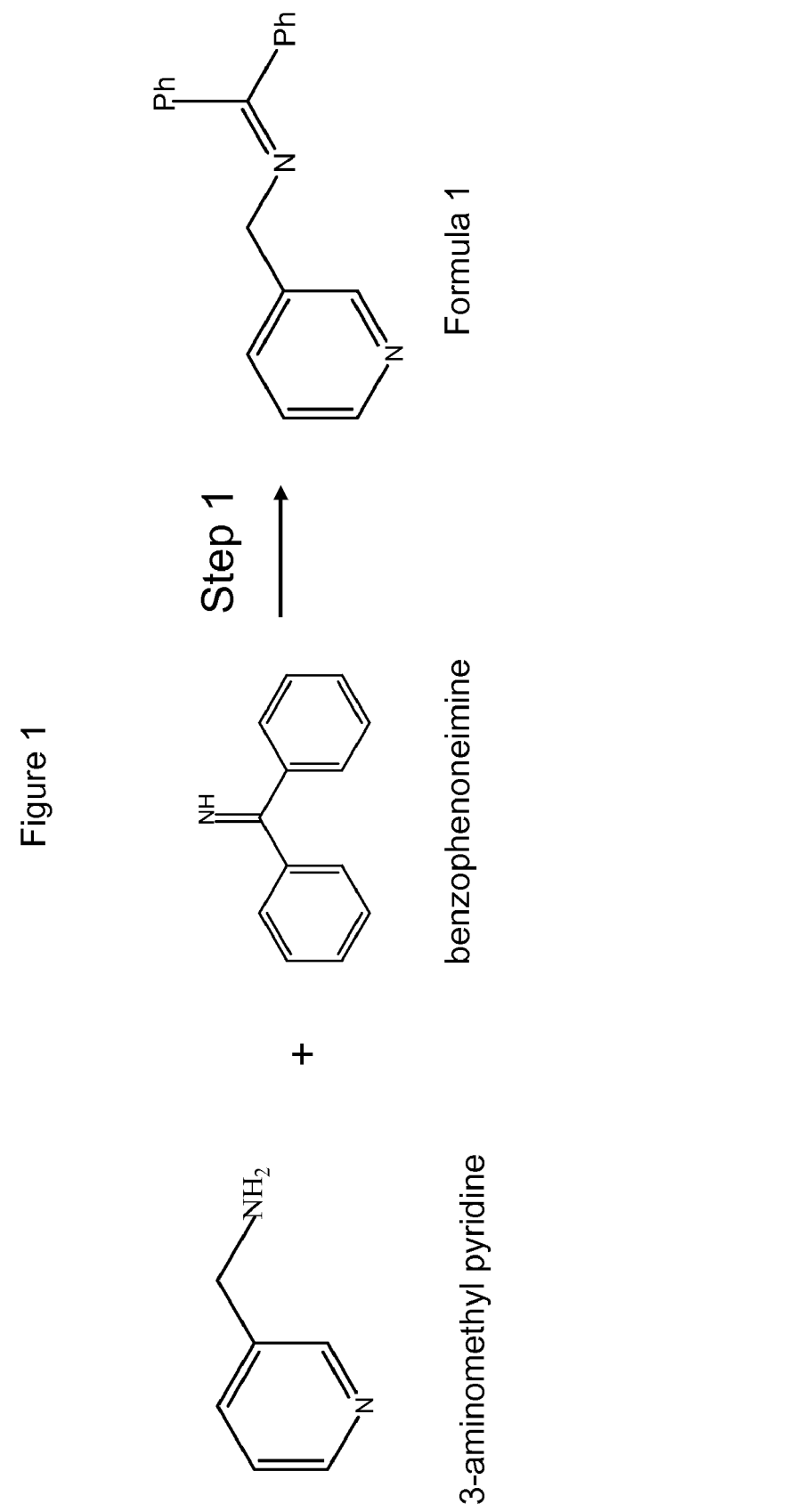
FIG. 1 illustrates 3-aminomethylpyridine reacted with benzophenoneimine to generate the α-alkylated imine of Formula I (benzylhydrylidene-pyridin-3-yl-methyl-amine).

The present invention relates to improved methods of synthesizing anatabine, especially methods that are useful in larger scale syntheses. In Step 1 (FIG. 1) 3-aminomethylpyridine is reacted with benzophenoneimine (or benzophenoneimine substituted in either or both rings with nitrogen, a halogen, or an alkyl group) to form benzylhydrylidene-pyridin-3-ylmethyl-amine, also referred to herein as Formula I:

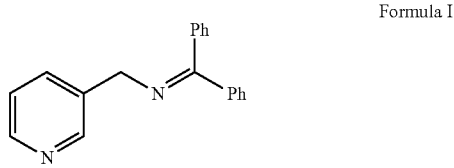

Formula I

Step 1 may be performed at any suitable temperature range. The reaction is exothermic, normally resulting in a temperature increase from ambient to about 45° C. to 55° C. If desired, the reaction mixture may be heated or cooled. In general, the rate of reaction increases at higher temperature and decreases at lower temperatures. For example, step 1 may be performed at about 30° C. to about 60° C. Most often, step 1 is performed at a temperature of about 45° C. to about 55° C.

The amount of time needed to complete Step 1 may vary depending on such factors such as reaction temperature and pressure. Normally, the reaction is completed in about 4 to about 9 hours, more usually from about 5 to about 7 hours.

Step 1 is particularly advantageous as it can be scaled up to facilitate larger scale production. For example, the amount of starting material (e.g. combined weight of 3-aminomethylpyridine and benzophenoneimine) used for a batch may be about 500 mg, about 1 g, about 5 g, about 10 g, about 20 g, about 25 g, about 30 g, about 40 g, about 50 g, about 100 g, about 200 g, about 500 g, about 1 kg, about 5 kg, or about 10 kg. Often, a medium scale synthesis starts with 20 g to 30 g of starting material. A large scale synthesis may start with 1 kg to 5 kg or more of starting material.

Using benzophenoneimine provides several key advantages over earlier methods and facilitates larger-scale synthesis as described above. First, the reaction by-product is ammonia rather than water. The ammonia escapes from the reaction mixture. By avoiding the presence of water as byproduct, the reaction temperature—50° C., for example—is much lower than the ~85° C. used for the water-removing benzene reflux step in the method of Deo et al. Using lower temperatures in the preparation of the compound offers improved economic and environmental efficiencies. Also, by omitting benzene from the reaction, the synthesis is safer and more environmentally-friendly. Avoiding the presence of water is also beneficial in terms of improved product stability because anatabine is moisture-sensitive.

Second, because benzophenoneimine is liquid, Step 1 may proceed in a solvent-less reaction medium such that the purity of the isolated intermediate is enhanced and avoids the need for a workup reaction. Purity of Formula I compound typically is about 93-95% whereas the Deo et al. method yields only about 83-85% purity of the intermediate.

The purity of Formula I compound may be as high as about 100%, about 99%, about 98%, about 97%, about 96%, about 95%, about 94%, or about 93%. Often, the Formula I compound is about 93% to about 95% pure.

In step 2i (FIG. 2) the compound of Formula I is reacted with a non-nucleophilic base, such as lithium diisopropylamide (LDA), and a dielectrophile, such as cis-1,4-dichloro-2-butene to form a compound of Formula II. The non-nucleophilic base typically is added in a molar excess, for example, at about 1.2 equivalents (eq), about 1.3 eq, about 1.4 eq, about 1.5 eq, about 1.6 eq, about 1.7 eq, about 1.8 eq, about 1.9 eq, or about 2.0 eq. Often the non-nucleophilic base is added in an amount of about 1.3 eq to about 1.7 eq, more usually from about 1.4 to about 1.6 eq.

The non-nucleophilic base is typically supplied in a chilled state to provide improved reagent stability. For example, LDA may be supplied at a temperature of about −30° C., about −20° C., about −10° C., about −5° C., about 0° C., about 5° C., or about 10° C. Most often the non-nucleophilic base is provided at a temperature of about −30° C. to about 0° C.

The Step 2i reaction may be incubated for a time suitable for the reaction to go to completion or substantial completion. For example, the reaction time for Step 2i often is about 10 minutes, about 20 minutes, about 30 minutes, about 40 minutes, about 50 minutes, or about 1 hour. Often, the reaction is incubated for about 20 to about 40 minutes.

As an alternative to LDA in step 2i, other strong bases such potassium tert butoxide ($K^tOBu$) may be used. Potassium tert butoxide ($K^tOBu$) was found to provide improved yield and purity. Using $K^tOBu$ we obtained an anatabine yield of 25% with 97% purity. Other alternatives to LDA include sodium hydride, sodamide, and other alkyllithium reagents.

Following addition of the non-nucleophilic base, a dielectrophile of Formula IV is added:

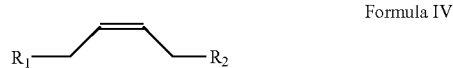

Formula IV wherein each of $R_1$ and $R_2$ is independently selected from the group consisting of chlorine, (Cl); bromine, (Br), and iodine, (I), tosylate, mesylate, and triflate. For example, $R_1$ and $R_2$ may both be Cl, such that the dielectrophile is cis-1,4-dichloro-2-butene. The dielectrophile may be added neat or in a suitable solvent, such as THF.

For step 2ii (FIG. 3) Formula II compound is hydrolyzed with acid. Treatment with acid may be for any suitable time. For example, HCl (10%) treatment may be for about 5 minutes, about 10 minutes, about 20 minutes, about 30 minutes, or for about 1 hour. Often, acid treatment is for about 10 minutes to about 20 minutes. Other suitable acids include dilute sulfuric acid and phosphoric acid. For step 2iii (FIG. 3), Formula III compound is basified, such as by treatment with solid $K_2CO_3$, then aqueous KOH solution (e.g., 40%) to achieve N-alkylation to yield anatabine. Other bases, such as Diaza(1,3)bicyclo[5.4.0]undecane (DBU), di-isopropyl ethylamine, or triethylamine, may also be used.

In another aspect, a method of recovering and purifying anatabine comprises extracting anatabine from the reaction product of Step 2iii using MTBE in a distillation process. The anatabine containing solution is basified to saturation with KOH and $K_2CO_3$. Addition of MTBE to the solution induces phase separation, with the anatabine separated into the organic phase, which provides an additional increase in anatabine purity. Subsequent distillation, followed by acid-base work up typically results in an anatabine purity of 99%.

Advantageously, this purification approach can be scaled up to industrial-scale manufacture. Purification by chromatography, which does not scale up from small-scale production, is avoided. Moreover, MTBE is more environmentally friendly than halogenated compounds such as chloroform. MTBE also improves extraction efficiency relative to halogenated compounds such as chloroform.

Anatabine prepared according to the methods disclosed herein displays good stability at a variety of temperatures. See, for example, Tables 3 and 4 in Examples 4 and 5, respectively. Purity of the anatabine may be retained for extended periods of time. For example, the anatabine may exhibit the indicated purity at 12 days, at 18 days, at 21 days, at 1 month, at 3 months, at 6 months, at 9 months, at 12 months at 18 months, at 24 months, and at 36 months, or longer. Further, anatabine remains stable when stored at a variety of temperatures. For example, the anatabine retains the indicated purity when stored at −20° C. to −10° C., −20° C. to 0° C., −10° C. to 0° C., 0° C. to 4° C., 2° C. to 8° C., 5° C. to 10° C., 10° C. to 15° C., 15° C. to 25° C., or 25° C. to 28° C. Stability is determined by any suitable art-recognized method. For example, anatabine stability may be monitored by high performance liquid chromatography (HPLC), liquid chromatography-mass spectroscopy (LC-MS), or nuclear magnetic resonance (NMR).

The synthesis described herein may yield significantly lower concentrations of byproducts, such as benzophenone, which can lower reaction yields and introduce impurities into the product. Concentrations of benzophenone, for example, are typically less than about 3% as compared to 8-12% that were found when reproducing the Deo et al. synthesis. Moreover, yield was 25% for the present invention but only 10% for the Deo et al synthesis.

In another aspect, acceptable pharmaceutical or food grade salts of anatabine are provided using an appropriate synthesis technique. Anatabine salts may provide improved chemical and chiral purity relative to the synthetic racemic alternative. Non-limiting examples of acceptable pharmaceutical or food grade salts that may be produced include tartrate, citrate, L-aspartate, camphor-10-sulphonate, cinnamate, cyclamate, fumarate, D-gluconate, L-glutamate, L-(+)-lactate, (±)-DL-lactate, maleate, malate, oxalate, galactarate, glucoheptonate, hippurate, malonate, (±)-DL-mandelate, nicotinate, salicylate, or succinate.

Figure 4:
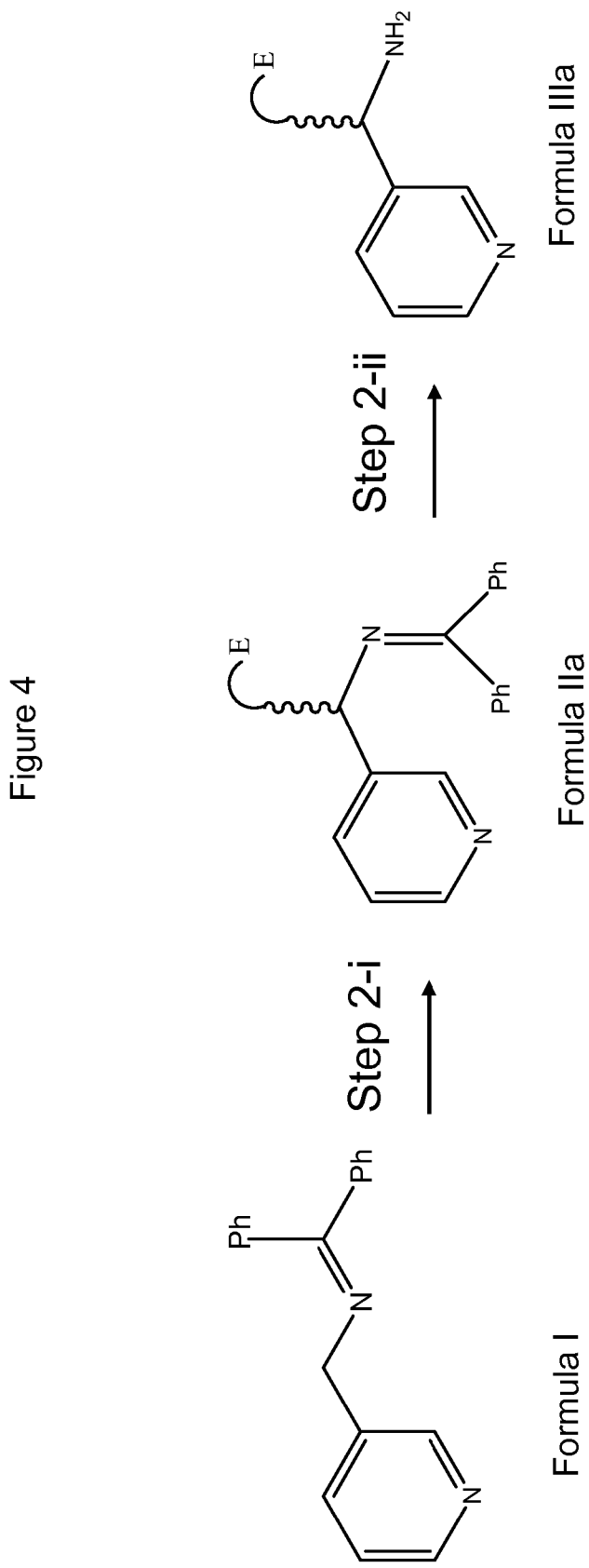
FIG. 4 illustrates an alternative embodiment in which a method for synthesizing other minor alkaloids is provided.

In an alternative embodiment, methods are provided for synthesizing other minor alkaloids, such as anabasine, nornicotine, N-methylanabasine, or anabaseine. With reference to FIG. 4, a compound of Formula I may be prepared as previously described and reacted with a dielectrophile to yield a compound of Formula IIa:

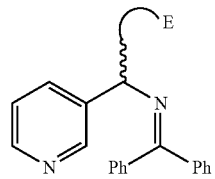

Formula IIa

The dielectrophile may be selected according to the desired alkaloid. For example, as described in Deo et al., anabasine may be synthesized using 1,4-diiodo-butane; nornicotine may be synthesized using 1,3-diiodo-propane or methanesulfonic acid 4-ethoxy-butyl ester, and so on. The compound of Formula IIa is then acidified as previously described to yield a compound of Formula IIIa.

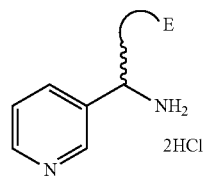

Formula IIIa

Basification of the compound of Formula IIIa results in the desired alkaloid by intramolecular N-alkylation as previously described.

The synthetic alkaloids may be provided in a variety of compositions. For example, the compositions may be in the form of a beverage, a chew, a tablet, a lozenge, a gum, and the like. Additional inactive ingredients may be added to improve taste or stability. Optionally, other components such as sweetening and flavoring agents may be added. Other active ingredients may be provided as well.

Compositions may be formulated together with one or more acceptable pharmaceutical or food grade carriers or excipients.

As used herein, the term "acceptable pharmaceutical or food grade carrier or excipient" means a non-toxic, inert solid, semisolid or liquid filler, diluent, encapsulating material or formulation auxiliary of any type. For example, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compositions may be administered by any suitable route. For example, the compositions may be administered orally, parenterally, by inhalation spray, topically, rectally, nasally, buccally, vaginally, via an implanted reservoir, or ingested as a dietary supplement or food. The term parenteral as used herein includes subcutaneous, intracutaneous, intravenous, intramuscular, and intracranial injection or infusion techniques. Most often, the compositions are administered orally and ingested.

The compositions may contain any conventional non-toxic pharmaceutically-acceptable carriers, adjuvants or vehicles. In some cases, the pH of the formulation may be adjusted with acceptable pharmaceutical or food grade acids, bases or buffers to enhance the stability of the formulated composition or its delivery form.

Liquid dosage forms for oral administration include acceptable pharmaceutical or food grade emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylsulfoxide (DMSO) dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, lozenges, pills, powders, and granules. In such solid dosage forms, the active compound is mixed with at least one inert, acceptable pharmaceutical or food grade excipient or carrier such as sodium citrate or dicalcium phosphate and/or a) fillers or extenders such as starches, lactose, sucrose, glucose, mannitol, and silicic acid, b) binders such as carboxymethylcellulose, alginates, gelatin, polyvinylpyrrolidone, sucrose and acacia, c) humectants such as glycerol, d) disintegrating agents such as agaragar, calcium carbonate, potato or tapioca starch, alginic acid, certain silicates, and sodium carbonate, e) solution retarding agents such as paraffin, f) absorption accelerators such as quaternary ammonium compounds, g) wetting agents such as cetyl alcohol and glycerol monostearate, h) absorbents such as kaolin and bentonite clay, i) lubricants such as talc, calcium stearate, magnesium stearate, solid polyethylene glycols, sodium lauryl sulfate, and mixtures thereof, and j) sweetening, flavoring, perfuming agents, and mixtures thereof. In the case of capsules, lozenges, tablets and pills, the dosage form may also comprise buffering agents.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract or, optionally, in a delayed manner. Examples of embedding compositions which can be used include polymeric substances and waxes. Tablet formulations for slow release are also described in U.S. Pat. No. 5,942,244.

In order to prolong the effect of a substance, it is often desirable to slow the absorption of the substance from subcutaneous or intramuscular injection. This may be accomplished by the use of a liquid suspension of crystalline or amorphous material with poor water solubility. The rate of absorption of the substance then depends upon its rate of dissolution, which, in turn, may depend upon crystal size and crystalline form. Alternatively, delayed absorption of a parenterally administered substance form is accomplished by dissolving or suspending the substance in an oil vehicle. Injectable depot forms are made by forming microencapsule matrices of the substance in biodegradable polymers such as polylactide-polyglycolide. Depending upon the ratio of substance to polymer and the nature of the particular polymer employed, the rate of substance release can be controlled. Examples of other biodegradable polymers include poly (orthoesters) and poly(anhydrides). Extended release formulations are known in the art. For example, swellable particles are taught in U.S. Pat. Nos. 5,582,837, 5,972,389, and 6,723,340. Polymer matrices are taught in U.S. Pat. Nos. 6,210,710, 6,217,903, and 6,090,411. Typical materials used for extended release formulations are the polymers poly(ethylene oxide) and hydroxypropyl methylcellulose. Depot injectable formulations are also prepared by entrapping the substance in liposomes or microemulsions that are compatible with body tissues.

The contents of each of the above cited journal articles and patents are hereby incorporated by reference as if set forth fully herein.

EXAMPLE 1

Step 1. Preparation of Formula I 3-aminomethylpyridine was added to neat benzophenoneimine (1 eq), according to FIG. 1. The reaction was allowed to proceed for 6 hours at 50° C. providing Formula I as the product.

EXAMPLE 2

Steps 2i to 2iii: Conversion of Formula I to Anatabine using Potassium Tert Butoxide (K$^t$OBu)

Step 2i: To Formula I of Example 1 was added K$^t$OBu (1.5 eq) in THF at −78° C. to −45° C. and the reaction was incubated for 30 min. Cis-1,4-dichloro-2-butene in 3 vol of THF at −78° C. was added, and the temperature was allowed to warm to −45° C. The reaction was allowed to proceed at −45° C. for 1-2 hours, providing Formula II. Optionally, the starting material may be added to the K$^t$OBu.

Figure 3:
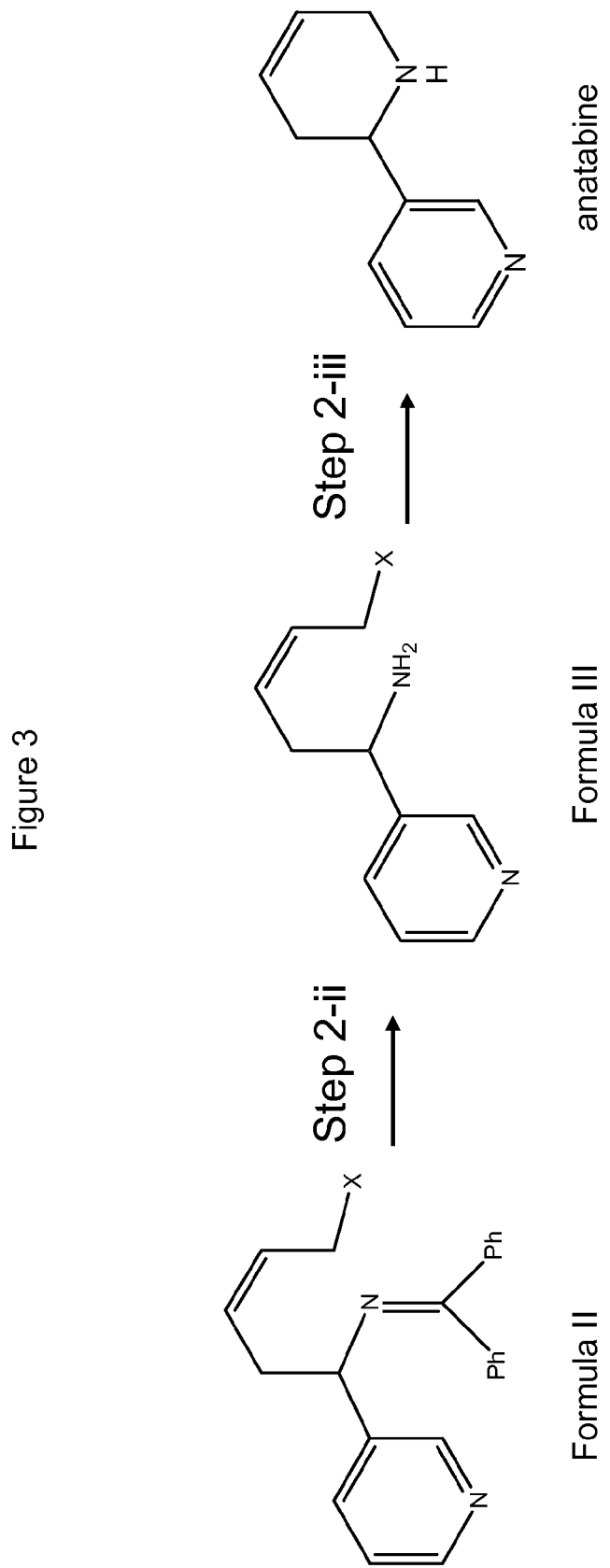
FIG. 3 illustrates steps 2ii and 2iii of the reaction. Step 2i: Formula II compound is converted to Formula III compound by acid hydrolysis. Step 2iii: Formula III compound is converted to anatabine by basification.

Step 2ii: 10% aqueous hydrochloric acid was added to the solution containing Formula II for 10-20 minutes to provide Formula III. (FIG. 3).

Step 2iii: The Formula III solution was basified by adding K$_2$CO$_3$ then treated with a 40% aqueous KOH solution to provide anatabine. (FIG. 3).

Results from different batches are show in Table 1.

TABLE 1

| Batch No. and amount | Reaction Conditions | Yield | Comments |
|---|---|---|---|
| A (2 g) | i) K$^t$OBu (1.1 eq), THF,-78° C. to −45° C. for 30 min ii)cis-1,4-dichloro-2-butene −45° C. for 1-2 h iii) 10% aq HCl, 10-20 min, ether wash. iv) K$_2$CO$_3$, 40% aqueous KOH | 0.7 g (crude) | SM was added to K$^t$OBu. 64.52% of Step 2i product Anatabine 65.12% pure by HPLC |
| B (2 g) | i) K$^t$OBu (1.5 eq), THF, −78° C. to −45° C. for 30 min ii)cis-1,4-dichloro-2-butene −45° C. for 1-2 h iii) 10% aq HCl, 10-20 min, ether wash. iv) K$_2$CO$_3$, 40% aqueous KOH | 0.68 g (crude) | Note that 1.5 eq of K$^t$OBu was used. 70.32% of Step 2i product Anatabine 67.06% pure by HPLC |

TABLE 1-continued

| Batch No. and amount | Reaction Conditions | Yield | Comments |
|---|---|---|---|
| C (25 g) | i) K'OBu (1.1 eq), THF, −78° C. to −45° C. for 30 min<br>ii) cis-1,4-dichloro-2-butene −45° C. for 1-2 h<br>iii) 10% aq HCl, 10-20 min, ether wash.<br>iv) K₂CO₃, 40% aqueous KOH | 8.5 g (crude) | 50% of Step 2i product Anatabine 57.7% pure by HPLC |

EXAMPLE 3

Steps 2i to 2iii alternate route: Conversion of Formula I to Anatabine using LDA Formula I was prepared according to Example 1. LDA was added to Formula I at −10 to 0° C. Cis-1,4-dichloro-2-butene was added at −78° C. to −45° C. Steps 2ii and 2iii were performed according to Example 2.

TABLE 2

| Batch No. and amount | Reaction Conditions | Yield | Comments |
|---|---|---|---|
| D (25 g) | i) LDA (1.2 eq), THF, −30° C. to 0° C. for 30 min<br>ii) cis-1,4-dichloro-2-butene −78° C. to −45° C. for 1-2 h<br>iii) 10% aq HCl, 10-20 min, ether wash.<br>iv) K₂CO₃, 40% aqueous KOH | 6.9 g (crude) | 71% conversion in IPC. 23.14% SM was seen in Step 2i. 72.64% purity by HPLC. |
| E (5 g) | i) LDA (1.5 eq) −30° C. to 0° C. for 30 min<br>ii) cis-1,4-dichloro-2-butene −78° C. to −45° C. for 1-2 h<br>iii) 10% aq HCl, 10-20 min, ether wash.<br>iv) K₂CO₃, 40% aqueous KOH | — | 80% conversion in IPC Anatabine 70.6% pure by HPLC |
| F (25 g) | i) LDA (2.0 eq), −30° C. to 0° C. for 30 min<br>ii) cis-1,4-dichloro-2-butene −78° C. to −45° C. for 1-2 h<br>iii) 10% aq HCl, 10-20 min, ether wash.<br>iv) K₂CO₃, 40% aqueous KOH | — | 67% conversion in IPC Anatabine 76.1% pure by HPLC |
| G (25 g) | i) LDA (1.5 eq), −30° C. to 0° C. for 30 min<br>ii) cis-1,4-dichloro-2-butene −78° C. to −45° C. for 1-2 h<br>iii) 10% aq HCl, 10-20 min, ether wash.<br>iv) K₂CO₃, 40% aqueous KOH | | Anatabine 73.7% pure by HPLC |

EXAMPLE 3A

Recovery/Purification of Anatabine Using MTBE and Distillation

The product of Example 2, Step 2iii was extracted with methyl t-butyl ether (MTBE), followed by distillation of the solvent and product distillation using a glass distillation assembly. Optionally, for scale-up, wiped film or thin film evaporation may be used. Yield of step 2 was 40%; overall yield was 26%.

COMPARATIVE EXAMPLE 3A

Recovery/Purification of Anatabine Using Chloroform Column Chromatography

The product of Step 2iii was treated with chloroform extraction as described in Deo et al. Chloroform extraction resulted in an anatabine yield of 10%.

EXAMPLE 4

Stability Analysis of Formula I.

Several batches of Formula I produced by reacting benzophenoneimine with aminomethylpyridine in the absence of benzene were stored refrigerated and also at room temperature. Testing by HPLC shows that purity was constant when refrigerated and only deviated 1-2% at room temperature.

TABLE 3

| Days | Purity (%) (stored at 2-8° C.) | Purity (%) (stored at 25-28° C.) |
|---|---|---|
| 1 | 88.61 | 88.93 |
| 2 | 88.83 | 85.49 |
| 3 | 88.30 | 88.02 |
| 6 | 88.83 | 86.62 |
| 12 | 88.75 | 87.47 |
| 18 | 88.46 | 87.25 |

EXAMPLE 5

Stability Analysis of Anatabine Base with and without BHT as a Preservative

Anatabine base stability was analyzed with and without BHT (3,5-di-tert-butyl-4-hydroxytoluene). The initial purity of BHT-free anatabine base was 94.95%. The initial purity of anatabine base with BHT was 94.87%. Anatabine stability, with and without BHT is reported in Table 4

TABLE 4

| Day | Storage Temperature | Purity (%) (with BHT) | Purity (%) (without BHT) |
|---|---|---|---|
| 1 | 25-28° C. | 93.27 | 89.63 |
|   | 2-8° C. | 93.26 | 94.44 |
|   | −20° C. | 94.26 | 93.90 |
| 2 | 25-28° C. | 92.73 | 87.59 |
|   | 2-8° C. | 94.83 | 94.05 |
|   | −20° C. | 94.73 | 94.62 |
| 3 | 25-28° C. | 87.44 | 80.74 |
|   | 2-8° C. | 94.26 | 91.65 |
|   | −20° C. | 94.62 | 93.87 |
| 12 | 25-28° C. | 85.10 | 79.59 |
|   | 2-8° C. | 94.18 | 90.12 |
|   | −20° C. | 94.74 | 94.01 |

EXAMPLE 6

Preparation of Anatabine Salts

To a solution of anatabine (4.0 g, 24.9 mmol) in acetone (20 ml), L-(+)-tartaric acid (3.37, 22.4 mmol) was added at room temperature. The reaction mass was warmed to 50° C. for 16 hours. The supernatant was decanted and the solid was triturated with diethyl ether (20 ml), filtered and dried under vacuum.

TABLE 5

| Solvent Used | Anatabine Tartrate (% Purity by HPLC) |
|---|---|
| Isopropyl alcohol | >94% |
| Acetone | >99% |

To a solution of anatabine (0.47 g, 2.9 mmol) in acetone (3 ml), citric acid (0.5 g, 2.6 mmol) was added at room temperature under a nitrogen atmosphere. The reaction mass was warmed to 50° C. for 16 hours. The supernatant was decanted and the solid was triturated with diethyl ether (20 ml), filtered and dried under vacuum.

TABLE 6

| Solvent Used | Anatabine Citrate (% Purity by HPLC) |
|---|---|
| Acetone | >97% |

While particular embodiments have been described and illustrated, it should be understood that the invention is not limited thereto since modifications may be made by persons skilled in the art. The present application contemplates any and all modifications that fall within the spirit and scope of the underlying invention disclosed and claimed herein.

What is claimed is:

1. A method of synthesizing anatabine comprising the steps of:
    (a) reacting 3-aminomethyl pyridine with benzophenonimine to obtain a compound of Formula I:

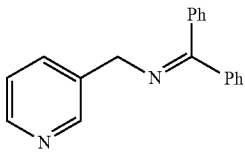

Formula I (b) reacting the compound of Formula I with a non-nucleophilic base and a dielectrophile to obtain a compound of Formula II:

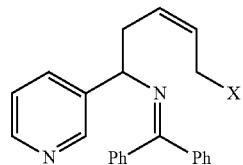

Formula II wherein X is a halogen,
    (c) treating the compound of Formula II with an acid to obtain a compound of Formula III:

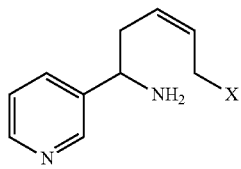

wherein X is a halogen; and
    (d) treating the compound of Formula III with at least one base to obtain anatabine.

2. The method of claim 1, further comprising extracting the reaction product obtained in step (d) with methyl tert-butyl ether (MTBE) solvent and removing the solvent by distillation to recover purified anatabine.

* * * * *